United States Patent
Meller

(10) Patent No.: US 6,791,676 B1
(45) Date of Patent: Sep. 14, 2004

(54) SPECTROPHOTOMETRIC AND NEPHELOMETRIC DETECTION UNIT

(75) Inventor: Paul Meller, Wehrheim (DE)

(73) Assignee: Dade Behring Marburg GmbH, Marburg (DE)

( * ) Notice: Subject to any disclaimer, the term of this patent is extended or adjusted under 35 U.S.C. 154(b) by 128 days.

(21) Appl. No.: 09/680,436

(22) Filed: Oct. 6, 2000

(30) Foreign Application Priority Data

Oct. 8, 1999 (DE) ......................................... 199 48 587

(51) Int. Cl.[7] ............................................. G01N 21/00
(52) U.S. Cl. ........................ 356/73; 356/416; 356/337
(58) Field of Search ............................. 356/72–73, 311, 356/319–320, 337, 339, 416, 417

(56) References Cited

U.S. PATENT DOCUMENTS

| | | | |
|---|---|---|---|
| 3,832,062 A | * | 8/1974 | Van Den Bosch .......... 356/323 |
| 3,990,851 A | | 11/1976 | Gross et al. |
| 4,053,229 A | | 10/1977 | McCluney |
| 4,325,910 A | | 4/1982 | Jordan |
| 4,408,880 A | | 10/1983 | Tsuji et al. |
| 4,692,883 A | * | 9/1987 | Nelson et al. .............. 436/517 |
| 4,730,922 A | | 3/1988 | Bach et al. |
| 4,889,815 A | * | 12/1989 | Bradwell et al. ........... 356/440 |
| 5,104,218 A | * | 4/1992 | Garner ......................... 356/73 |
| 5,400,137 A | | 3/1995 | Winslow et al. |
| 5,959,738 A | * | 9/1999 | Hafeman et al. ............. 356/73 |
| 6,042,785 A | * | 3/2000 | Harju ......................... 356/317 |
| 6,096,561 A | * | 8/2000 | Tayi ........................... 436/518 |
| 6,104,945 A | * | 8/2000 | Modell et al. ........... 250/252.1 |
| 6,175,750 B1 | * | 1/2001 | Cook et al. .............. 250/252.1 |

FOREIGN PATENT DOCUMENTS

| | | | |
|---|---|---|---|
| DE | 2409273 A1 | 4/1975 | |
| EP | 997726 A2 | 5/2000 | |
| FR | 2792725 | 10/2000 | |
| WO | WO 86/07454 | * 12/1986 | .......... G01N/21/25 |
| WO | WO 98/00701 | 1/1998 | |

OTHER PUBLICATIONS

Marmer, et al., "Nephelometric and Turbidimetric Immunoassay," Immunoassay (1996) Academic Press, Inc , pp 363–387.

English Language Derwent Abstract for EP 997726 A2.

English Language Derwent Abstract for FR 2792725.

* cited by examiner

Primary Examiner—F. L. Evans
Assistant Examiner—Kara Geisel
(74) Attorney, Agent, or Firm—Finnegan, Henderson, Farabow, Garrett and Dunner, L.L.P.

(57) ABSTRACT

A method and apparatus for spectrophotometric and/or nephelometric analyses. The apparatus can be used in in-vitro diagnosis.

37 Claims, 3 Drawing Sheets

SPECTROPHOTOMETRIC AND NEPHELOMETRIC DETECTION UNIT

The present invention relates to a method and an apparatus for the essentially simultaneous performance of spectrophotometric and nephelometric analyses principally in in-vitro diagnosis.

While on the one hand an increasing demand for more sensitive optical detection methods for automated in-vitro laboratory analysis has evolved in recent years, at the same time requirements for increasing alignment and harmonization of the analytical methods have been instituted.

These requirements can be comprehended against the background of the concentration of the number of measurement laboratories in the form of a few centers for laboratory diagnosis. Only by more extensively matching the analytical methods and reducing the number of different equipment variants or method conditions can the tests be carried out simply and without increased operational requirements. These endeavors are thereby intended to result in further cost savings in the field of diagnosis.

The need for more complex, fully automated analysis equipment is growing at the same time. In order to be able to process a multiplicity of different samples and types of samples and to achieve the required throughput, said analysis equipment is additionally coupled via corresponding networks to laboratory integration systems for discontinuous tracking of sample, test or consumable material.

Capital expenditure and subsequent capacity utilization of such fully automated analysis machines can only be achieved, however, if at the same time there is also harmonization in analysis in the different fields of application of in-vitro diagnosis. Thus, even now, attempts are being made to implement inter alia parameters of clinical chemistry, plasma protein diagnosis or immunochemical diagnosis on common platforms. This is successful particularly when the requirements made of the process technology in the different fields of application are similar. This is because the conditions for the treatment of samples or of reagents solutions with regard to storage (temperature stability) or metering (volume, precision) often correspond well.

Thus, the increasing matching and harmonization should also consistently extend to the detection methods used for analysis.

Most of the analytical methods employed at the present time only use a way of obtaining measurement data of the kind offered by photometry or light scattering. In certain analysis methods, the light scattering is detected at different angles or under different angular ranges. Scattered-light methods are extremely sensitive and their resolution is superior to that of photometric methods particularly for methods in which the formation and temporal change of scattering centers are detected, as is the case in agglutination tests or in methods of particle-enhanced in-vitro diagnosis. Comprehensive considerations and calculations concerning the theory of scattered light are adequately known per se to the person skilled in the art and are textbook material (thus, for example, C. F. Bohren, D. R. Huffman, Absorption and Scattering of Light by Small Particles, J. Wiley & Sons, 1983). Further aspects of application to in-vitro diagnosis tests may be found inter alia in E. P. Diamandis et al. 1997 (Immunoassay, Academic Press, 1997, Chapter 17: Nephelometric and Turbidimetric Immunoassay) and the references cited therein.

On the other hand, the requirement for many test methods consists of carrying out photometric tests which purely detect absorption. The scattered-light signal fails in these cases since, at best, the contaminants contained in the material to be measured can be measured.

By way of example, DE-A 2409273 and U.S. Pat. No. 4,408,880 describe methods in which a sample is excited by a laser beam and its scattered light is detected at an angle outside the beam axis of the incident light. The scattered light used for the measurement is masked out by a suitably shaped annular diaphragm which retains the excitation light from the laser.

U.S. Pat. No. 4,053,229 likewise describes an apparatus for measuring scattered light, in which a scattered light measurement is effected simultaneously at an angle of 2° and at an angle of 90°.

WO 98/00701 describes a combination of a nephelometer with a turbidimeter which comprises two light sources. While one of these, in the form of a laser, produces the scattered light which is detected at 90°, a diode (LED) emitting in the infrared spectral region serves for measuring the turbidity on the axis of the incident light. The method described in the application serves in particular for improved control of the intensity of the laser used.

To date, there are no known methods and/or apparatuses which enable both scattered-light measurements and photometric measurements to be carried out essentially simultaneously.

The present invention was thus based on the object of finding an apparatus permitting essentially simultaneous spectrophotometric and nephelometric measurement in a sample within one assembly.

Essentially simultaneous means that the measurement points of the spectrophotometric determination and those of the nephelometric determination succeed one another in time as closely as is necessary for the type of measurement. In the case of kinetic measurements, the time interval will need to be shorter than, for example, in the case of end point measurements in which the time interval of the measurements is essentially determined by the mechanical size of the rotational/translational movement of the measurement cell in relation to the measurement location. In the case of kinetic measurements, on the other hand, the time interval must be as short as possible.

The present invention describes an apparatus allowing a combination of methods for carrying out in-vitro diagnosis analyses based on the principle of scattered-light measurement and of spectrophotometry.

In this case, the measurement unit enables methods of photometry and of scattered-light measurement to be employed essentially simultaneously. Light from one or more light sources 1, 2 is guided via one or more light guidance arrangements 3 to the common beam axis 24 and then via the common beam axis to the reaction location 11. Scattered light or photometric signal can be detected by means of sensors 17 and a spectrophotometer 25. Pulse driving means that the two methods are decoupled temporally such that no reciprocal influencing or interference occurs during operation.

While nephelometry is used predominantly for the analysis of agglutination tests and in particle-enhanced immunodiagnosis, photometry serves for measuring numerous other clinical-chemical parameters based on spectral changes. The combination makes it possible to achieve the aim of being able to carry out a multiplicity of different diagnostic tests pertaining to clinical chemistry, immunodiagnosis, plasma protein diagnosis or coagulation diagnosis on a single module. The present description relates to the field of the use of automated measurement systems in analysis and in in-vitro diagnosis. In particular, the apparatus described makes it possible to simultaneously carry out tests which are measured with the aid of scattered-light measurement and/or by photometry in the UV-Vis spectral region.

In particular, the unit can be integrated in systems in which the measurement of a multiplicity of samples and tests in measurement cuvettes is carried out on a common rotor or carousel, as is often the case for automatic analysis systems.

The invention has developed an apparatus which makes it possible to measure both the scattered light from a sample, which is produced at angles outside the axis of the incident light, and the light transmitted at angles around 0°.

Different narrowband or broadband light sources can be used to excite the material to be measured. These are guided on a common beam guidance arrangement to the reaction location. The pulsed driving of the light sources enables mutual disturbances or interference to be completely suppressed.

It is likewise an aim of the method described to carry out a validation of the beam path and the components used, such as the light source, the optical components of lenses and diaphragms and the properties brought about by the moving accommodating vessels of the material to be measured (cuvettes).

The method according to the invention and an apparatus are explained in more detail below by way of example using just one embodiment.

FIG. 1 schematically shows an arrangement of light sources 1, 2, reaction location 11 for material to be measured (e.g., a cuvette) and a sensor 17, a sensor for reference measurement 22, and a spectrophotometer 25. As is evident from this, solid angles around the axis of the incident light are utilized in both methods. In the arrangement used most for scattered-light measurement, the scattered light is detected at an angle of 90°. Separation of the incident light from the scattered light is particularly easy to achieve as a result. On the other hand, choosing a larger solid-angle range and utilizing angles or angular ranges around the forward direction of the incident light make it possible to achieve higher intensities of the scattered light, as a result of which an arrangement can be constructed in a technically simple and more cost-effective manner. The proportion of scattered light at angles around the forward direction is particularly high precisely for the measurements (which are striven for in accordance with the present description) on organic macromolecules with utilization of a particle-enhanced immunoassay for use in human in-vitro diagnosis.

The light sources 1, 2 employed for the analysis have different spectral bandwidths in accordance with the application which is striven for. While a light source for the scattered-light measurement has a narrowband emission in the red or infrared spectral region, preferably in the range between 600 and 950 nm, the light source for photometric measurements typically emits in a spectral region between 300 and 800 nm. Both light sources are used in pulsed operation in the present embodiment.

For the purpose of common beam guidance and excitation of a material to be measured 12 contained in the reaction location 11, the light from both light sources 1, 2 is guided to a coupling unit 4 for example via optical waveguides or bundles of fibers and is coupled out via suitable optical components. A dichroic beam splitter 5 specifically adapted for the two bandwidths enables both light sources to be guided on the common beam axis 24. Corresponding lenses 6, 9 are used to collimate the beam for the later measurement. A fraction of the incident lights can be masked out, by means of a further beam splitter 8, for the reference measurement by a sensor for reference measurement 22, and optionally using an PD converter 23.

The light beam following the common beam axis 24 impinging through a diaphragm 10 on the material 12 to be measured which is situated in a reaction location 11 leads to scattering or absorption, depending on the type of material to be measured.

However, the pulsed excitation of the two light sources means that both methods can be carried out independently of one another. The information which is necessary for triggering one of the light sources can in this case be chosen by way of a test definition, which is necessary prior to the measurement, and is thus known to the system while the measurement is being carried out.

The physical separation of the axially transmitted and of the scattered light 20 is effected by a diaphragm 13 arranged on the beam axis. In this case, the diaphragm is advantageously configured in such a way that it serves on the one hand as a scattered light trap and on the other hand as a deflection unit for the axially incident light. To that end, the diaphragm is constructed as an annular and perforated diaphragm. By the choice of an internal and external diameter, it is possible to select the most favorable solid-angle range for the analysis. The proportion which is transmitted as scattered light through the diaphragm is focused onto the input of a detector 17 by means of a lens or a lens system 14.

While the scattered light measurement usually involves a discrete, narrowband wavelength, a broader-band light source is used for the photometric measurement, with the result that the signal used for a photometric measurement should be evaluated further. For this purpose, the light impinging on the beam axis around 0° is coupled out with the aid of the diaphragm 13, the central part of which is designed as a perforated diaphragm. The latter preferably has a diameter of from 0.5 to 3 mm, which limits the incident beam cross-section. In this case, the beam can be deflected by a beam deflection arrangement such as a prism 18 or another suitable light guidance system, such as a correspondingly curved bundle of fibers, for example. The light is coupled into the bundle 19 of fibers by means of the optical components known to the person skilled in the art. The bundle of fibers subsequently serves as entrance slit of a spectrophotometer 25. In this case, the known principle of a diode linear array is used as the spectrophotometer and, equipped with no mechanical components, allows a short measurement time with a full spectral bandwidth.

After the signal has been evaluated and the spectrum $i=f(\lambda)$ has been obtained, the data are fed to a computer 27 for further processing.

According to the invention, the arrangement described is frequently employed in analysis systems in which, for an increased throughput, a multiplicity of measurement cuvettes are to be processed simultaneously. For this purpose, the cuvettes are positioned on a rotatable carousel or rotor, as evident from FIG. 3, for example. This likewise clarifies the favorable mode of use of the pulsed operation in accordance with FIG. 2: if a reaction location 11 is situated in the region 32, 34 which is accessible to the measurement optics within a time interval $\Delta 1$, a pulse ($\Delta 2$) from one of the available light sources 1, 2 can be triggered, and is applied to the reaction location 11 and a beam guidance arrangement 33 and the coupling unit 32. The signal obtained from this is detected within the time interval $\Delta 4$. Depending on the type of test and associated evaluation method, the transmitted or scattered proportion of the light is detected by the sensors 17 and 22, respectively. The type of driving thus permits completely separate excitation of the material to be measured by the different light sources and exhibits no mutual influencing of the scattered or of the transmitted light. An additional time interval Δ3 illustrated in FIG. 2 serves for the possible detection of a reference signal by sensor 17 and 22 for the adjustment of a dark value.

By cyclically rotating a carousel 31 equipped with cuvettes, it is possible to measure a subsequent cuvette.

In addition to these two primary methods, a host of possibilities may be opened up in which the two methods complement one another:

1. Calibration of the light source by the spectrophotometer 25: the momentary introduction of a standard 7 into the beam path can be used for determination of the wavelengths or absorption.

2. Testing the positioning of a cuvette situated in the region of the measurement unit: cyclic movement of a cuvette situated on the rotor enables the recording of a location-dependent cuvette profile and the further position determination thereof.

3. Fluorescence/chemiluminescence mode: a material 12 to be measured which is situated in the cuvette 11 can be selectively excited by means of one of the light sources 1, 2, if appropriate with the utilization of further filters 7. By means of the detector 17, the resulting fluorescent light can be detected, under certain circumstances by the use of further blocking filters 15.

LIST OF REFERENCE SYMBOLS FOR THE FIGURES

Figure 1:
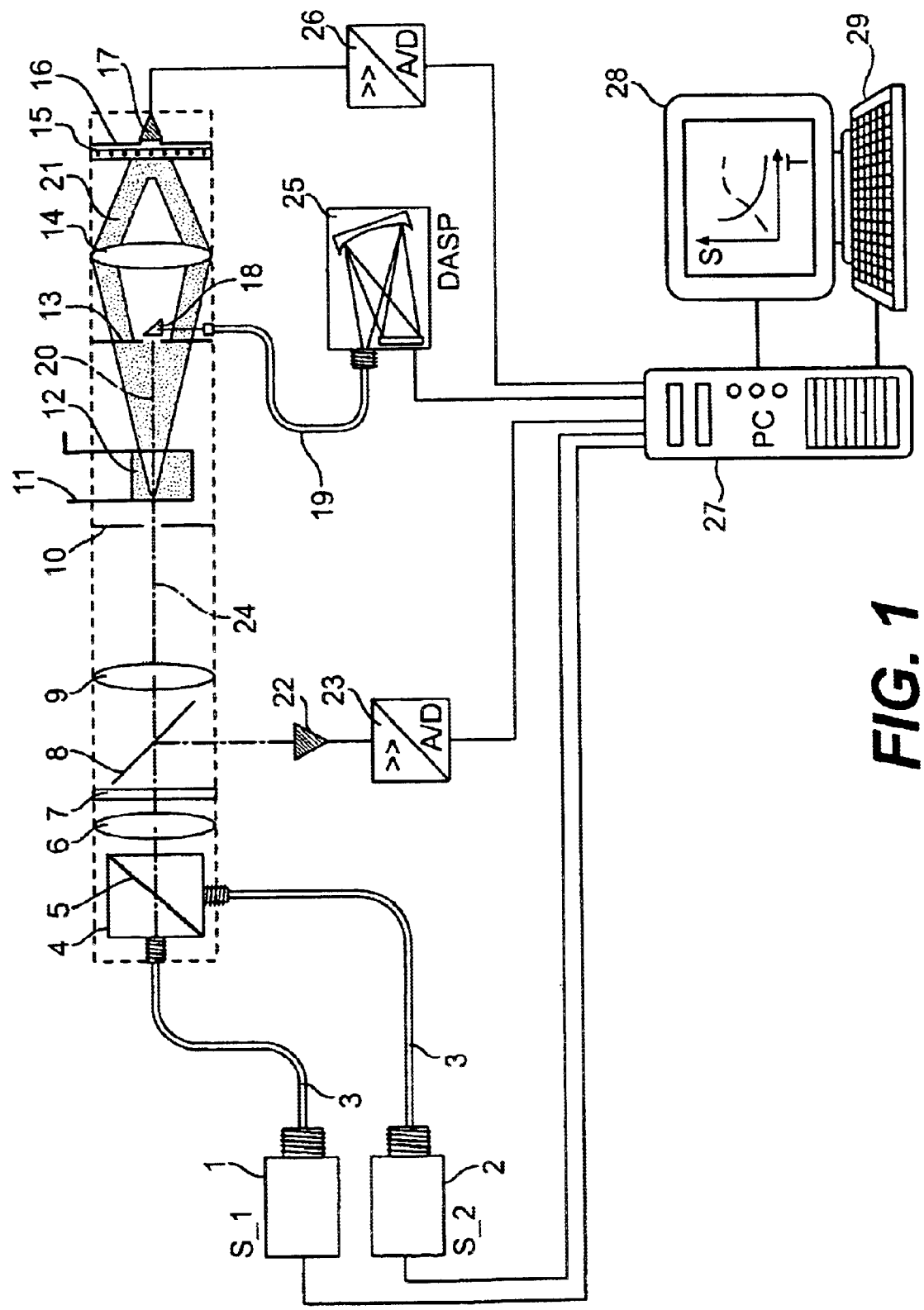
FIG. 1 shows a schematic overview of an embodiment of the analysis unit which is described in more detail below.
Figure 2:
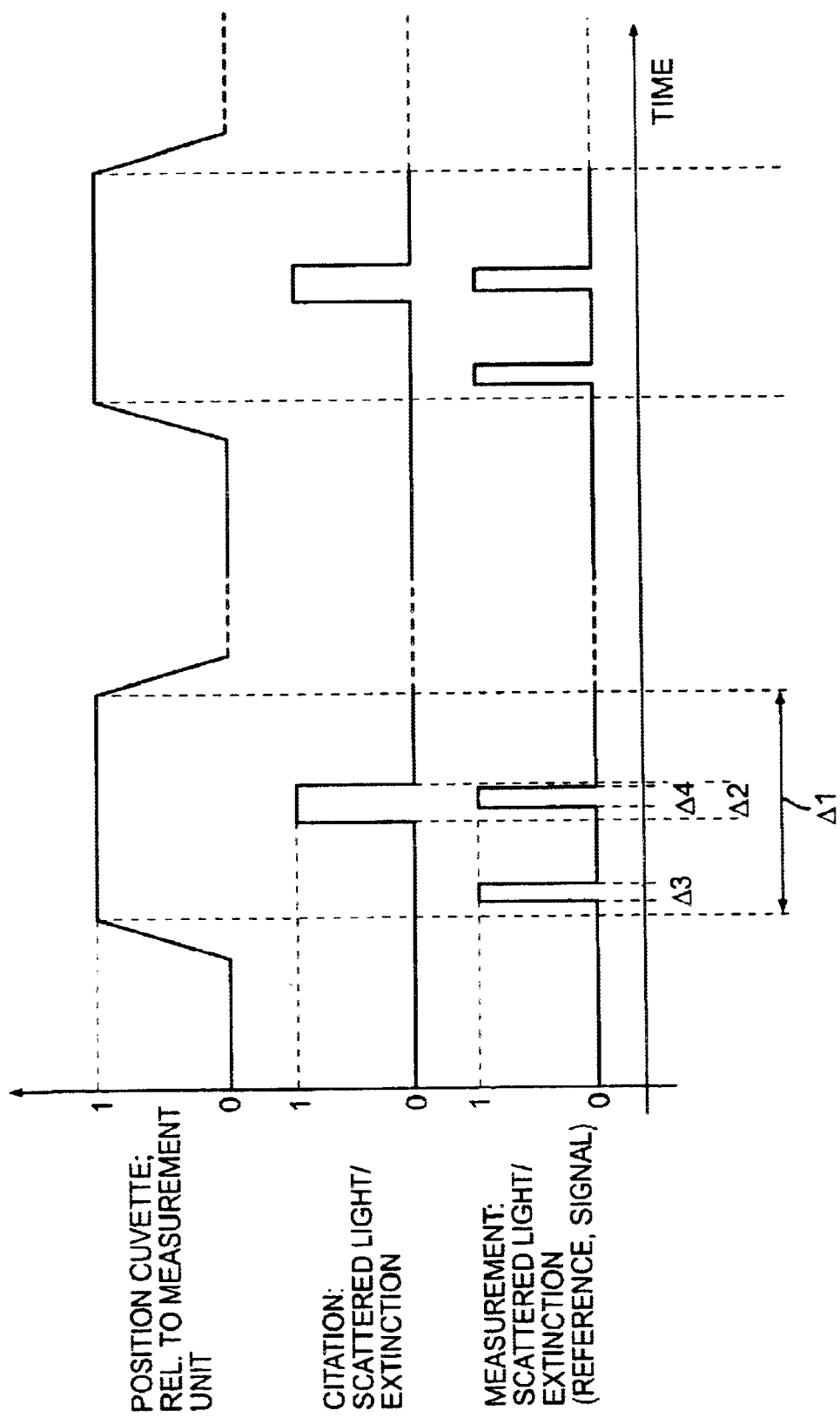
FIG. 2 represents a timing diagram of the driving of the different light sources and the recording of measured values.
Figure 3:
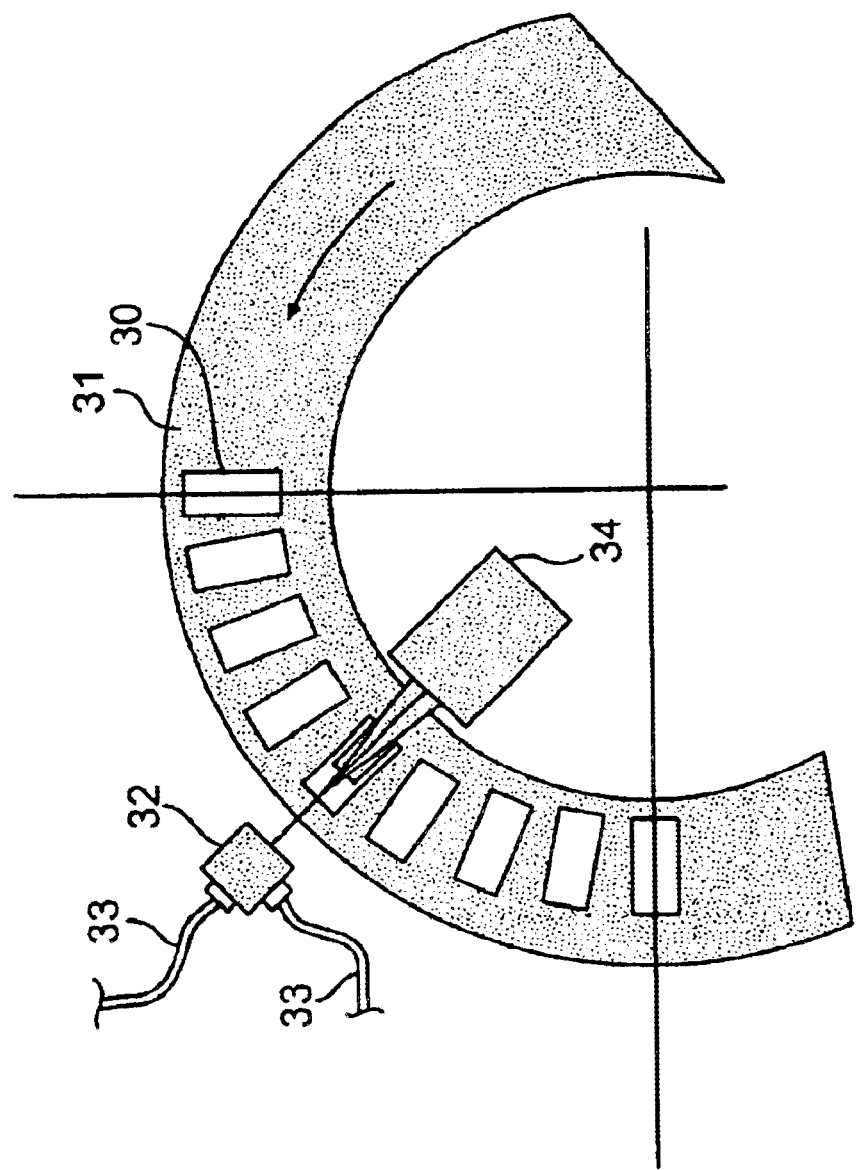
FIG. 3 shows the use of the measurement unit within a rotatable rotor for accommodating a multiplicity of measurement cuvettes arranged in a circle.

1. Light source 1
2. Light source 2
3. Light guidance arrangement (bundle of fibers)
4. Coupling unit
5. Beam splitter (dichroic)
6. Lens system/lens 1
7. Filter
8. Beam splitter
9. Lens system/lens 2
10. Diaphragm
11. Cuvette/reaction location
12. Material to be measured
13. Diaphragm
14. Lens system/lens
15. Blocking filter
16. Diaphragm
17. Sensor/detector
18. Beam deflection arrangement (e.g. prism)
19. Bundle of fibers/optical waveguide coupling
20. Light emerging from cuvette
21. Scattered light
22. Sensor for reference measurement
23. A/D converter
24. Common beam axis
25. Spectrophotometer
26. A/D converter
27. Computer
28. Screen
29. Keyboard
30. Cuvette/reaction location
31. Carousel/rotor for accommodating cuvettes
32. Illumination unit with optical waveguide coupling on arrangement
33. Beam guidance arrangement
34. Detection unit

What is claimed is:

1. A method for analyzing a sample, comprising:

providing two light sources;

coupling light emitted from the two light sources into a common beam;

guiding the common beam through a sample to be analyzed to generate a first signal and a second signal different from the first signal;

detecting the first signal impinging at small angles around the common beam to obtain a nephelometric measurement of the sample; and detecting the second signal to obtain a spectrophotometric measurement of the sample.

2. The method of claim 1, wherein providing the two light sources includes providing first and second light sources.

3. The method of claim 2, wherein providing the first and second light sources includes providing the first light source having a first spectral bandwidth and the second light source having a second spectral bandwidth different from the first bandwidth.

4. The method of claim 3, wherein providing the first light source includes providing the first having a narrow band emission in one of the red and infrared spectral regions.

5. The method of claim 4, wherein the narrow band emission is in the range between 650 nm and 950 nm.

6. The method of claim 3, wherein providing the second light source includes providing the second light source having an emission band of between 300 nm and 800 nm in the spectral regions.

7. The method of claim 2, wherein one of the first and second light sources is in the ultraviolet spectral region.

8. The method of claim 2, wherein at least one of the first and second light sources is a xenon pulsed light.

9. The method of claim 2, wherein one of the first and second light sources is a light-emitting diode.

10. The method of claim 9, wherein the light-emitting diode emits light in the spectral regions ranging from 800 nm to 950 nm.

11. The method of claim 2, further comprising pulsing at least one of the first and second light sources.

12. The method of claim 1, wherein providing the at least one light source includes pulsing the at least one light source.

13. The method of claim 1, wherein guiding the light emitted from the at least one light sources includes guiding the light through a filter.

14. The method of claim 13, wherein guiding the light emitted from the at least one light source further includes guiding the light through a diaphragm.

15. The method of claim 1, further comprising detecting the light for a reference signal.

16. The method of claim 1, further comprising deflecting light out of the common beam.

17. The method of claim 1, further comprising separating out light of an undesirable spectral region to suppress it.

18. The method of claim 1, further comprising exciting the sample to be analyzed with the light emitted from the two light sources.

19. The method of claim 1, further comprising calibrating wavelengths and absorptions of the light emitted from the light sources.

20. The method of claim 1, further comprising amplifying and converting at least one of the first and second signals.

21. The method of claim 1, further comprising commonly controlling detection, evaluation, and presentation of at least one of the first and second signals.

22. The method of claim 1, further comprising performing an in-vitro analysis.

23. The method of claim 1, further comprising changing the position of the sample to be analyzed.

24. A method for analyzing a sample, comprising:
providing two light sources;
coupling light emitted from the two light sources into a common beam;
masking out light impinging at small angles around the common beam;
guiding light emitted from the common beam through a sample to be analyzed to generate a first signal and a second signal different from the first signal; and
detecting the first signal to obtain a nephelometric measurement of the sample;
substantially simultaneously detecting the second signal to obtain a spectrophotometric measurement of the sample.

25. A method for analyzing a sample, comprising:
providing two light sources;
coupling light emitted from the two light sources into a common beam;
guiding light emitted from the common beam through a sample to be analyzed to generate a first signal and a second signal different from the first signal;
detecting light impinging at small angles around the common beam;
detecting the first signal to obtain a nephelometric measurement of the sample; and
substantially simultaneously detecting the second signal to obtain a spectrophotometric measurement of the sample.

26. A method for analyzing a sample, comprising:
providing two light sources;
coupling light emitted from the two light sources into a common beam;
guiding light emitted from the common beam through a sample to be analyzed to generate a first signal and a second signal different from the first signal;
detecting light at angles of less than 5 degrees around a forward direction of the common beam;
detecting the first signal to obtain a nephelometric measurement of the sample;
substantially simultaneously detecting the second signal to obtain a spectrophotometric measurement of the sample.

27. An apparatus for carrying out optical measurements, comprising:
two light sources;
means for coupling the light from the two light sources into a common beam;
means for guiding the common beam through a sample to be analyzed to generate a first signal and a second signal different from the first signal;
means for detecting the first signal impinging at small angles around the common beam to obtain a nephelometric measurement of the sample; and
means for detecting the second signal substantially simultaneously with detection of the first signal to obtain a spectrophotometric measurement of the sample.

28. The apparatus of claim 27, wherein the two lights sources having different spectral bandwidths.

29. The apparatus of claim 27, wherein one of the two light sources includes a narrow band emission in one of the red and infrared spectral regions.

30. The apparatus of claim 27, wherein one of the two light sources includes an emission in one of the ultraviolet and visible spectral regions.

31. The apparatus of claim 27, wherein the light emitted from at least one of the two light sources is a pulsed light.

32. The apparatus of claim 27, further comprising means for detecting the light for a reference signal.

33. The apparatus of claim 27, wherein the means for guiding light includes a filter.

34. The apparatus of claim 27, wherein the means for guiding light includes a diaphragm.

35. The apparatus of claim 27, further comprising means for deflecting light out of the common beam.

36. An apparatus for carrying out optical measurements, comprising:
two lights sources having different spectral bandwidths;
means for coupling the light from the two light sources into a common beam;
means for guiding light emitted from the two sources through a sample to be analyzed to generate a first signal and a second signal different from the first signal;
means for detecting the first signal to obtain a nephelometric measurement of the sample;
means for detecting the second signal substantially simultaneously with detection of the first signal to obtain a spectrophotometric measurement of the sample;
means for detecting the light for a reference signal; and
means for detecting light impinging at small angles around the common beam.

37. An apparatus for carrying out optical measurements comprising:
at least one light source having a spectral region;
at least one light guidance arrangement for guiding light from said at least one light source along a common beam axis intersecting at least one reaction location and positioned to receive the light from said at least one light source;
at least one filter for separation or combination of at least one desired spectral region and for beam shaping, wherein said at least one filter intersects said common beam axis and is positioned downstream from said at least one light guidance arrangement;
at least one diaphragm for limiting the beam diameter of said at least one light source and for shaping the beam, wherein said at least one diaphragm intersects said common beam axis and is positioned downstream from said at least one light guidance arrangement;
at least one sensor positioned to detect at least one signal generated by a material to be measured and at least one reference signal;
a second diaphragm for masking out the light impinging at small angles around said common beam axis, wherein said second diaphragm intersects said at least one common beam axis, is positioned downstream from said at least one light guidance arrangement, is for masking out the scattered-light impinging at small angles around the forward direction of said common beam axis, and is for transmitting light impinging at small angles around 0 degrees from the material to be measured and relative to said common beam axis for further measurement; and a beam deflection arrangement, comprising rigid optical components or an optical waveguide with corresponding connection components, positioned to guide out the impinging light from said common beam axis;

wherein the light is detected at angles of less than 5 degrees around the forward directions of said common beam axis and the detected light of said at least one signal is directed to an entrance slit of a spectrophotometric unit.

* * * * *